US00PP36101P2

(12) United States Plant Patent
Podaras

(10) Patent No.: US PP36,101 P2
(45) Date of Patent: Sep. 10, 2024

(54) ***WEIGELA* PLANT NAMED 'PODARASNWOW1'**

(50) Latin Name: *Weigela florida*
Varietal Denomination: PODARASNWOW1

(71) Applicant: Early Morning LLC, Greendale, IN (US)

(72) Inventor: Peter Podaras, Boring, OR (US)

(73) Assignee: Early Morning LLC, Greendale, IN (US)

( * ) Notice: Subject to any disclaimer, the term of this patent is extended or adjusted under 35 U.S.C. 154(b) by 45 days.

(21) Appl. No.: 18/371,719

(22) Filed: Sep. 22, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Karen M Redden
(74) *Attorney, Agent, or Firm* — Weatherly IP Solutions, LLC; James M. Weatherly

(57) ABSTRACT

A new cultivar of *Weigela* plant named 'PODARASNWOW1' that is characterized by a thin leaf variegation with a uniform green and white color, a compact and tight plant habit, and low seed set, is disclosed.

2 Drawing Sheets

Figure 1:
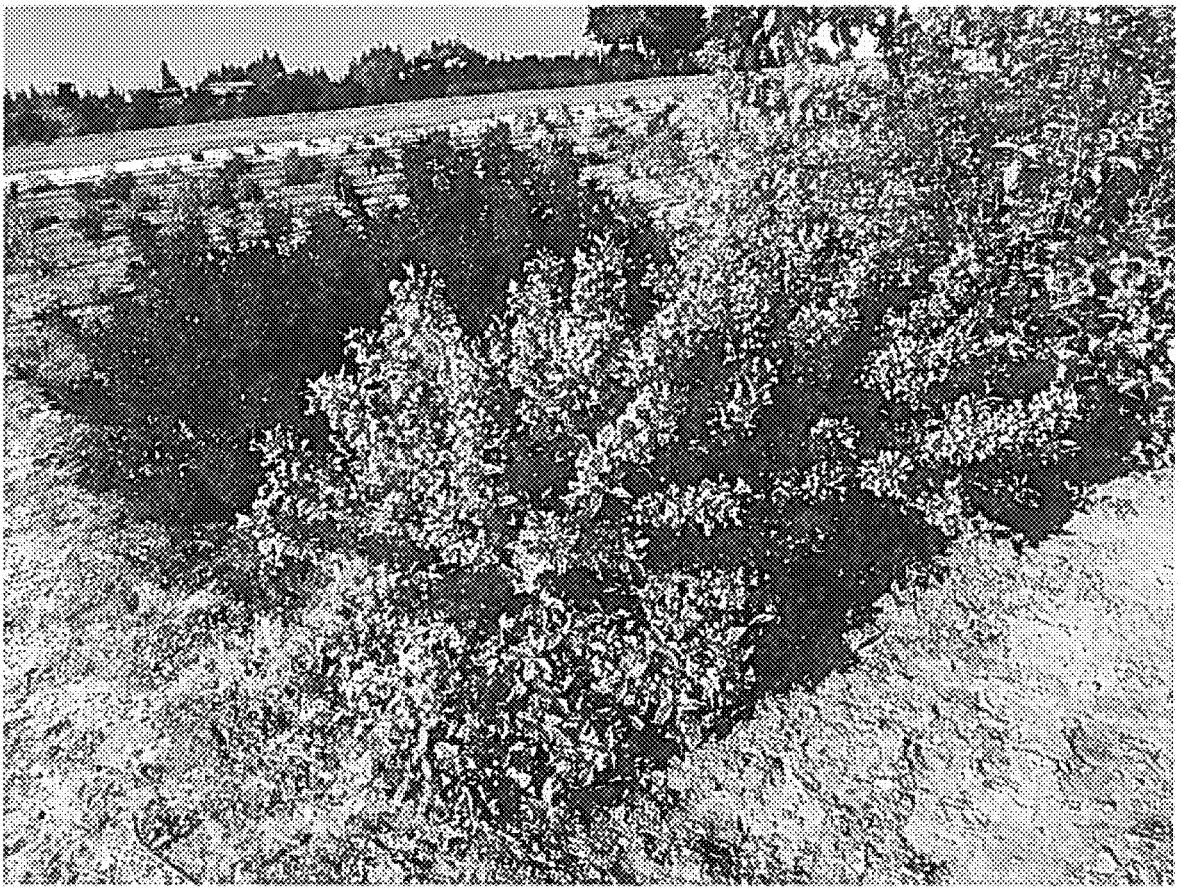

Genus and species: *Weigela florida.*
'PODARASNWOW1'.

BACKGROUND OF THE NEW PLANT

The present invention relates to a new and distinct cultivar of *Weigela*, grown as an ornamental plant for use in the garden and landscape. The process began when the *Weigela* variety 'Pink Poppet' (U.S. application Ser. No. 09/925,696) was crossed with *Weigela* 'Minuet' (not patented), and a small group of a dozen plants were grown. From one unnamed plant of the more compact individuals produced from the cross, open pollenated seed was collected in 2016.

Seed was then germinated in the winter of 2017 in Tipp City, Ohio. Out of several dozen seedlings, one was identified early in its development to have some variegation present on one of its leaves when about an inch and half high. This seedling was transplanted into a gallon container and grown to approximately the height of 10 inches.

At this point the plant was cut back two inches above the point where the variegated foliage was first noticed. As the plant resprouted from the axillary buds, one sprout associated with the variegated leaf, produced a perfect white marginally variegated shoot. As this shoot developed, the other non-variegated shoots were pinched and kept from overgrowing the variegated shoot. The next year following dormancy, the plant with the variegated shoot was allowed to flush out. The variegated shoot was stable and named 'PODARASNWOW1'. From there, the plant was upgraded to a 3-gallon pot and the non-variegated shoots were continually nipped back but not cut off so they could nourish the branch with the variegation.

In July of 2019, 30 cuttings of 'PODARASNWOW1' were made in Tipp City, Ohio. These were then transferred to Boring, Oregon in the Fall and planted into gallon containers the following Spring. Two were planted in the field and the remaining plants were upgraded to 3-gallon containers. As of 2023 all the plants retained their unique variegation. 'PODARASNWOW1' was found to reproduce true to type in successive generations of asexual propagation in Boring, Oregon via vegetative cuttings.

SUMMARY

The following traits have been repeatedly observed and represent the characteristics of the new *Weigela* cultivar 'PODARASNWOW1'. 'PODARASNWOW1' has not been tested under all possible conditions and phenotypic differences may be observed with variations in environmental, climatic and cultural conditions, however, without any variance in genotype.

Thin leaf variegation with a uniform green and white color;

Compact and tight plant habit; and

Low seed set.

BRIEF DESCRIPTION OF THE PHOTOGRAPHS

The accompanying color photographs illustrate the overall appearance of the new *Weigela* variety 'PODARASNWOW1' showing colors as true as it is reasonably possible to obtain in colored reproductions of this type. Colors in the photographs may differ from the color values cited in the detailed botanical description, which accurately describe the actual observed colors of 'PODARASNWOW1'. Photographs were taken on May 25, 2023 in Boring, Oregon.

FIG. 1 depicts two individuals planted side to side. The illustrated plants are three years old and have been grown entirely outdoors in Boring, Oregon. No chemicals were used to treat the plant.

Figure 2:
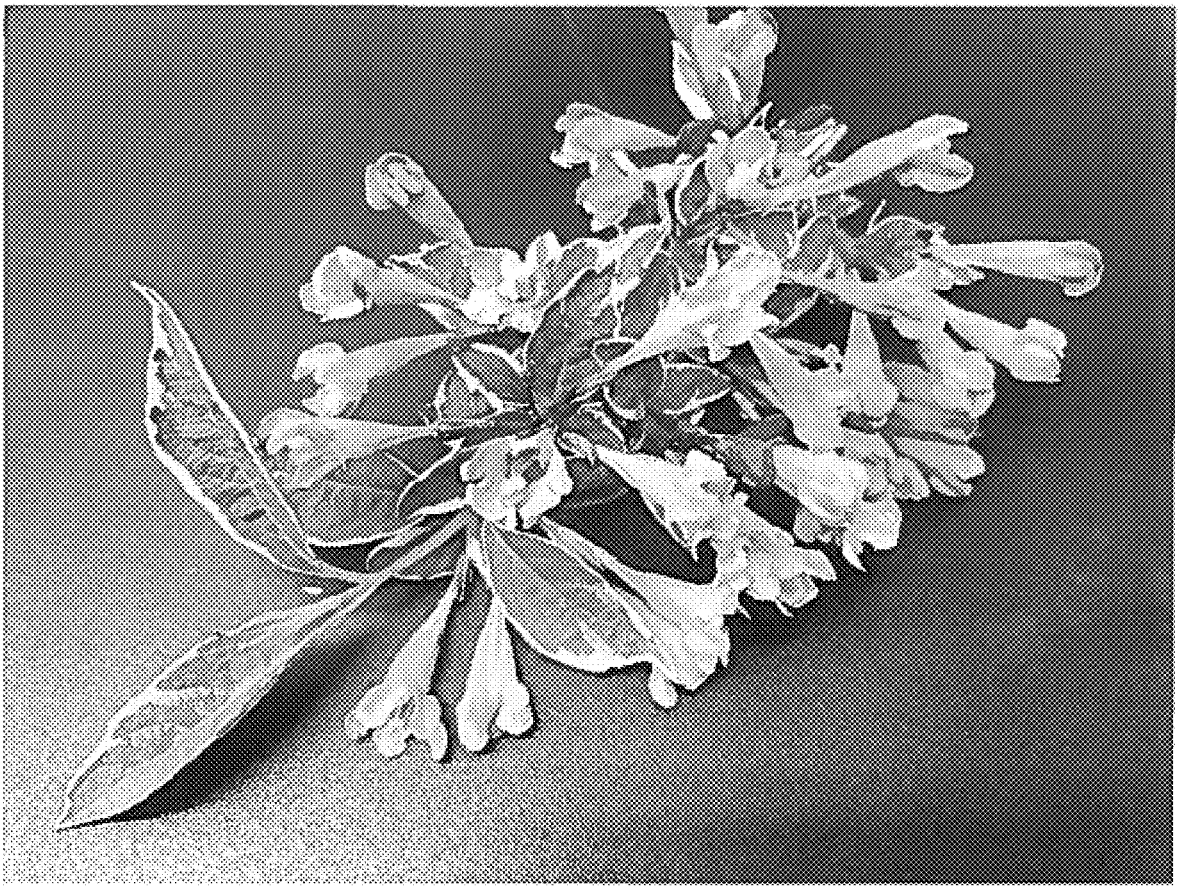

FIG. 2 depicts a close-up view of flowers and leaves.

BOTANICAL DESCRIPTION OF THE PLANT

The following is a detailed description of the new cultivar 'PODARASNWOW1'. Data was collected in late May 2023 from three years old plants in Boring, Oregon. The color determinations are in accordance with The R.H.S. Colour Chart 2001 and R.H.S. Mini Colour Chart 2005 of The Royal Horticultural Society, London, England, except where general color terms of ordinary dictionary significance are used. No chemicals were used to treat the plants. Growing conditions are typical of other *Weigela*.

Parentage:

*Female parent*.—Unnamed seedling of *Weigala* 'Pink Poppet' x W. 'Minuet'.

*Male parent*.—Unknown parent, open pollenated.

Classification:

*Family*.—Caprifoliaceae.

*Botanical*.—*Weigela* sp.

*Common*.—*Weigela*.

*Designation*.—'PODARASNWOW1'.

Plant description:

*Growth habit*.—Uniform, dense and round.

*Use*.—Foundation planting, low growing hedge or landscape accent.

*Suitable container sizes*.—1 gallon, 3 gallon or 5 gallon.

*Dimensions in second year in a 3-gallon container*.—2'×2'.

*Dimensions when mature in open ground*.—3.5'×3.5'.

*Hardiness*.—USDA 4.

*Propagation*.—Cutting with 2,500 ppm IBA.

*Time to initiate roots*.—2 to 3 weeks.

*Crop time*.—1 for a gallon, 2 years for 3 gallon.

*Roots*.—Description: Fibrous, densely branched. Color: RHS 155A (R.H.S. Mini Colour Chart 2005).

*Light*.—Full sun to as little as 4 hours direct sun.

*Soil type*.—Well drained.

*Seasonal interest*.—Spring: abundant flowering. Summer: variegated foliage.

Stem:

*Shape*.—Round and corky.

*Dimensions*.—Length: 110 cm. Diameter at soil level. 1.9 cm to 2.2 cm.

*Surface*.—RHS 199C.

*Lenticels*.—Description: Barely visible and only on newest shoots. The tendency to form a corky stem as stems mature make them impossible to distinguish. Diameter: 0.05 cm. Length: 0.1 cm to 0.15 cm. Color: RHS 145D.

Branches:

*Branch stem dimensions*.—Length: Total length 108 cm after 3 years. Diameter: 0.02 cm to 0.015 cm on current season growth.

*Internode length*.—2.6 cm.

*Color* (*current year's growth*).—RHS 176A to RHS 177A.

*Color* (*previous year's growth, lignified*).—RHS 156C.

*Surface pubescence*.—RHS 156C.

Foliage:

*Leaf arrangement*.—Opposite.

*Leaf division*.—Entire.

*Leaf shape*.—Lanceolate, shortly attenuate base and apiculate tip.

*Leaf attachment*.—

*Petiole dimensions*.—Length: 0.043 cm. Diameter: 0.018 cm.

*Leaf dimensions*.—Length: 6.1 cm. Width: 2.47 cm.

*Leaf surface* (*adaxial*).—Slightly waxy with impressed veins. Overall surface is slightly crinkled. Irregular white marginal variegation that is thickest at the mid sections along the length. Width of this variegation is 0.03 cm to 0.01 cm. Barely perceivable rose color in outer most margin of leaf.

*Leaf surface* (*abaxial*).—Smooth and dull.

*Leaf color* (*spring growth, adaxial surface*).—RHS 137B.

*Leaf color* (*spring growth, abaxial surface*).—RHS 138B.

*Leaf color* (*summer foliage, adaxial surface*).—Leaf color is RHS 137A (R.H.S. 2005 Colour Chart). Color of variegation is RHS 155D (R.H.S. 2005 Colour Chart) The faint rose color is too fine to measure reliably but possibly RHS 63A.

*Leaf color* (*summer foliage, abaxial surface*).—RHS 191B.

*Leaf apex*.—Acuminate hooking to slightly to one side. The opposite leaf will always hook in the opposite direction.

*Leaf base*.—Acute.

*Leaf margin*.—Crenulate.

*Leaf venation pattern*.—Reticulate.

*Veins* (*adaxial surface*).—RHS 152D.

*Veins* (*abaxial surface*).—RHS 152D.

Flowering time: Mid Spring.

Inflorescence:

*Fragrance*.—Faint but sweet.

*Inflorescence form*.—Corymb.

*Quantity of flowers per inflorescence*.—Ranges from groups of 6 to 18 with average containing about 10-12.

Flowers:

*Flower aspect*.—Salverform having 5 distinct lobes extending beyond the corolla tube. Two lobes are consistently closer together than the other three which gives the flower irregular symmetry.

*Diameter of fully developed flower* (*at flower tube apex*).—Open flower is 2.1 cm in diameter. Petals extend beyond the corolla tube reflexed at approximately 80 to 100 degrees for the two closer-spaced petals and 60-70 degrees for the other three.

Bud:

*Shape*.—Clavate.

*Color*.—RHS 64A for more immature and RHS 64B for buds closer to opening.

*Dimensions*.—Length: 2.5 cm to 2.7 cm. Diameter: 0.5 cm.

*Surface*.—Rugose to bullate and setulose, the bristles irregularly twisted or straighter the shorter they are.

Peduncle:

*Dimensions*.—Length 0.5 cm to 1 cm. Diameter: 0.1 cm to 0.2 cm.

*Shape*.—Rounded.

*Color*.—RHS 144A to RHS N77B.

*Surface*.—Irregularly setulose.

Calyx, sepals:

*Shape*.—Acute tip with irregularly incised margin.

*Calyx diameter*.—0.5 cm.

*Sepals*.—Sepals are partially fused into a calyx. Three sepals are fused together up to the halfway point along the length of the sepal. Two sepals are more fused than the other three at ⅔ to ¾ of the length of those sepals. Number: 5. Length: 1.1 cm. Width: 0.24 cm. Color: RHS 148C to RHS N77B. Surface: Upper: Bullate. Lower: Smooth.

Corolla:

*Shape*.—Salverform but almost bilabiate.

*Dimensions*.—Length: 3.5 cm. Diameter: 2.3 cm.

*Surface*.—Bullate.

*Tube color*.—Adaxial surface: RHS 77C. Abaxial surface: RHS 77B.

Petals:

*Number*.—5. Shape: All petals are rounded at their apex. Petal width is between 0.65 cm and 0.8 cm at the base are 1 cm to 1.2 cm long.

*Color* (*adaxial surface*).—RHS 76A and RHS 76B.

*Color* (*abaxial surface*).—RHS 77B and RHS 77C.

*Surface texture*.—Slightly bullate.

Reproductive organs:

*Number of stamens*.—5.

*Dimensions*.—Length: 0.3 cm to 0.4 cm. Diameter: 0.1 cm.

*Filament color*.—RHS 65C.

*Anther shape*.—Cuneate.

*Anther dimensions*.—Length: 0.3 cm to 0.4 cm. Width: 0.1 cm.

*Anther color*.—RHS 60 (R.H.S. 2005 Colour Chart).

*Pollen color*.—RHS 60 (R.H.S. 2005 Colour Chart).

*Pollen amount*.—Moderate.

*Number of pistils*.—1.

*Style*.—Shape: Filamentous. Length: 3 cm. Width: 0.15 cm. Color: RHS 155D (R.H.S. 2005 Colour Chart). Surface:

*Stigma shape*.—Bilobate.

*Stigma dimensions*.—Length: 0.4 cm. Width: 0.2 cm. Stigma color: RHS 145C (R.H.S. 2005 Colour Chart).

*Ovary*.—Inferior.

*Shape*.—Rod shaped with 5 barely distinguishable facets.

*Length*.—1 cm to 1.5 cm.

*Width*.—0.15 cm.

*Color*.—RHS N177A to RHS 147B.

Fruit: Poorly formed, mostly abortive.

Seed: Very little.

Susceptibility or resistance to pests and diseases: Very resistant compared to other variegated varieties.

COMPARISON OF 'PODARASNWOW1' WITH PARENTAL LINE AND KNOWN VARIETY

'PODARASNWOW1' is distinguished from the mutation parent as described in Table 1.

TABLE 1

Comparison with Parental Line

| Trait | Variety 'PODARASNWOW1' | Female parent | Male Parent |
|---|---|---|---|
| Leaf color | Green and white | Green | Green |
| height | 3.5' | 6' | 6' |
| habit | Compact and tight | Loose | Loose |

'PODARASNWOW1' can be compared to the commercial *Weigela* variety 'Rainbow Sensation' (not patented). Differences between the varieties are described in Table 2.

TABLE 2

Comparison with Similar Variety

| Trait | Variety 'PODARASNWOW1' | Commercial line 'Rainbow Sensation' |
|---|---|---|
| Variegation | Variegation is thinner than Rainbow Sensation with a yellow-green color | Variegation is thicker and yellowish with shades of rose |
| Seed set | None to Low | Very high |
| Babit | Uniform, dense, rounded, strong upright branches | Loose with floppier branching with more open habit |
| Disease resistance | Very resistant to foliar diseases | Poor resistance to foliar damage from disease |

I claim:

1. A new and distinct cultivar of *Weigela* plant named 'PODARASNWOW1' as described and illustrated herein.

* * * * *